United States Patent
Huynh et al.

(10) Patent No.: US 8,954,281 B2
(45) Date of Patent: Feb. 10, 2015

(54) WELLBORE FLUID TESTING APPARATUS AND METHODS

(75) Inventors: Huy Huynh, Houston, TX (US);
Kenneth Slater, Sealy, TX (US)

(73) Assignee: M-I L.L.C., Houston, TX (US)

( * ) Notice: Subject to any disclaimer, the term of this patent is extended or adjusted under 35 U.S.C. 154(b) by 743 days.

(21) Appl. No.: 13/147,889

(22) PCT Filed: Feb. 11, 2010

(86) PCT No.: PCT/US2010/023870
§ 371 (c)(1),
(2), (4) Date: Aug. 4, 2011

(87) PCT Pub. No.: WO2010/093774
PCT Pub. Date: Aug. 19, 2010

(65) Prior Publication Data
US 2011/0295509 A1    Dec. 1, 2011

Related U.S. Application Data

(60) Provisional application No. 61/151,706, filed on Feb. 11, 2009.

(51) Int. Cl.
*G01N 15/08* (2006.01)
*E21B 21/00* (2006.01)

(52) U.S. Cl.
CPC ........................ *E21B 21/00* (2013.01)
USPC ........................................................... 702/12

(58) Field of Classification Search
CPC ........................................................ E21B 21/01
USPC ........................................................... 702/12
See application file for complete search history.

(56) References Cited

U.S. PATENT DOCUMENTS

| | | | |
|---|---|---|---|
| 5,309,761 | A | 5/1994 | Ravi et al. |
| 5,438,169 | A | 8/1995 | Kennedy et al. |
| 2007/0289734 | A1 | 12/2007 | McDonald et al. |
| 2008/0236253 | A1 | 10/2008 | Tehrani et al. |

FOREIGN PATENT DOCUMENTS

| | | |
|---|---|---|
| WO | 2008058253 A2 | 5/2008 |
| WO | 2008-112795 A1 | 9/2008 |
| WO | 2008-118953 A1 | 10/2008 |

OTHER PUBLICATIONS

International Search Report and Written Opinion for PCT/US2010/023870.
Aston, et al., "A New Treatment for Wellbore Strengthening in Shale", SPE 110713 - SPE Annual Technical Conference and Exhibition, Anaheim, Ca, 2007, pp. 1-7.
Raghavan, et al., "Chapter 8: Gel Formation: Phase Diagrams Using Tabletop Rheology and Calorimetry", Springer, the Netherlands, 2005, pp. 233-244.

*Primary Examiner* — Stephen Cherry

(57) ABSTRACT

A system for testing a wellbore fluid includes a test chamber having first and second platens therein. The chamber is in a thermally insulating enclosure. The enclosure includes a heating element. The platens simulate response of the wellbore fluid through an hydraulically induced fracture in subsurface rock formation. The system includes means to control a distance between the platens. A pump introduces the wellbore fluid into a space between the platens and another pump introduces a pressure test fluid into contact with the wellbore fluid. A respective pressure sensor is in fluid communication with a discharge side of each pump, and a sensor is included to measure a parameter related to the position of the second platen or the space between the platens. A data acquisition and control device is configured to detect signals from the respective pressure transducers and the sensor.

28 Claims, 7 Drawing Sheets

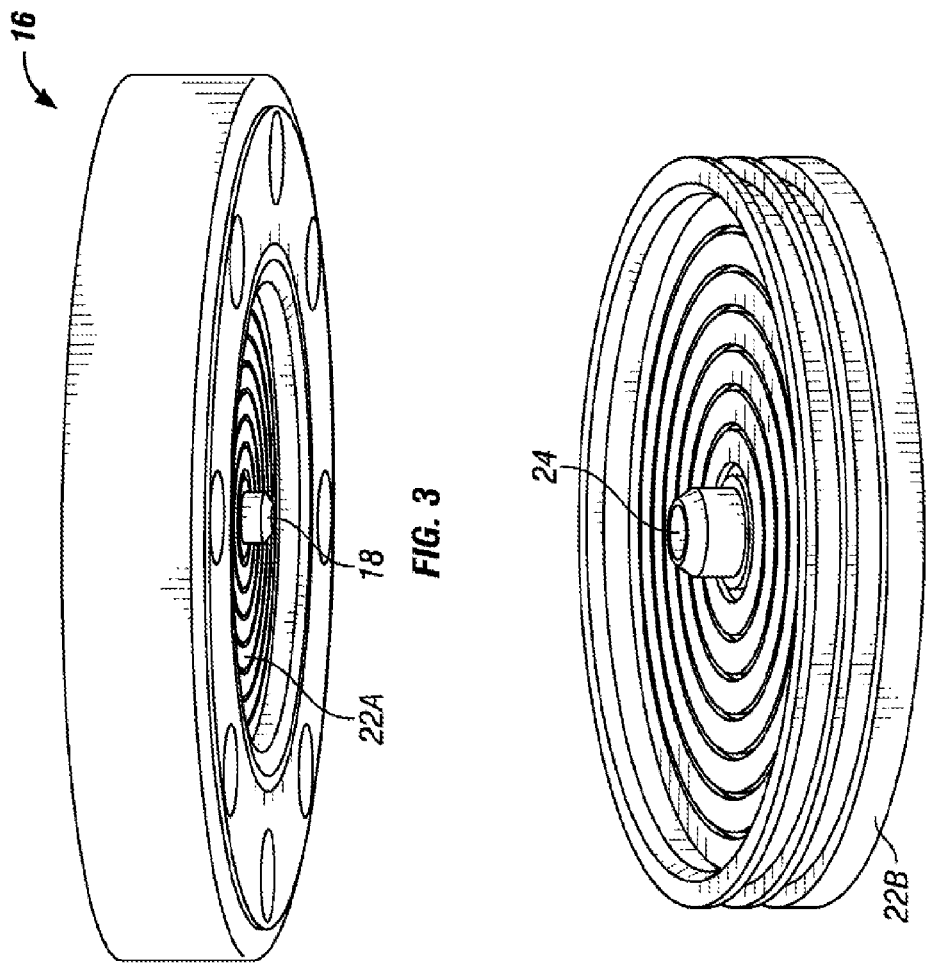
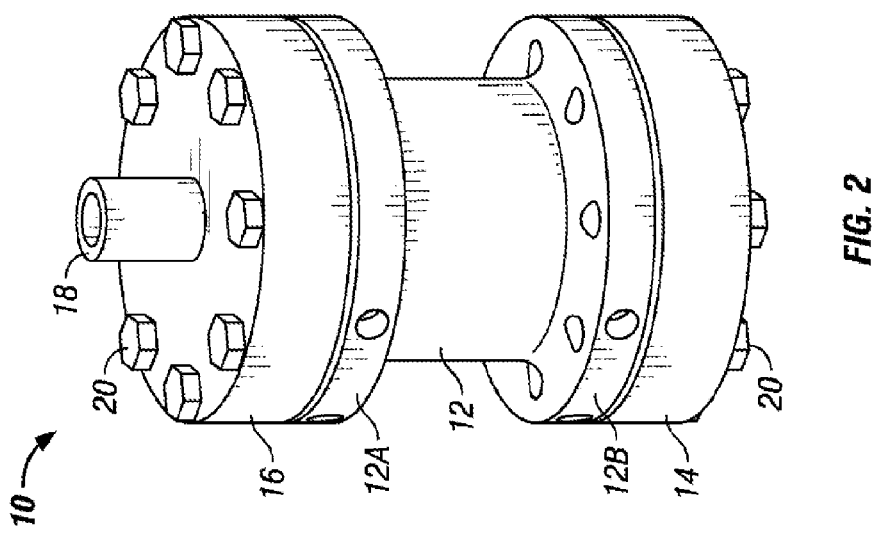

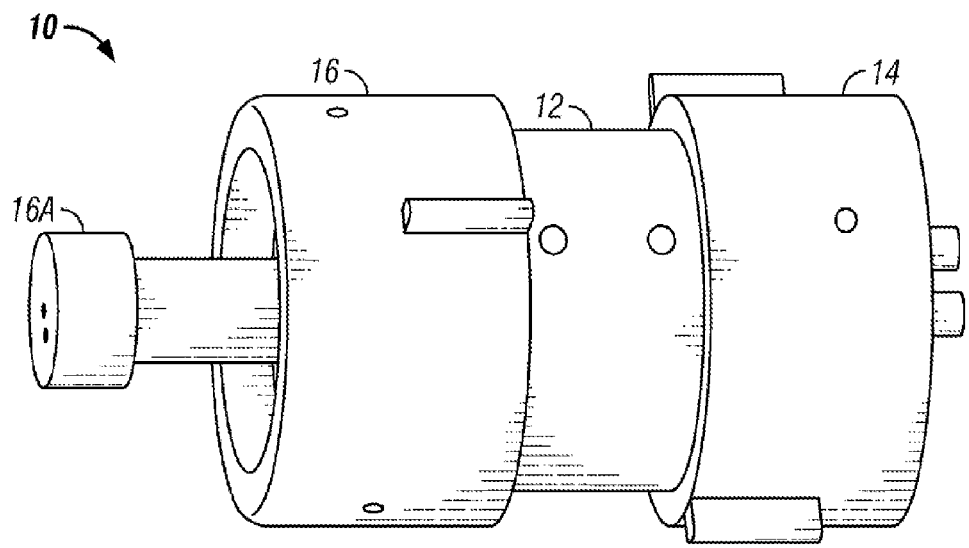
FIG. 5
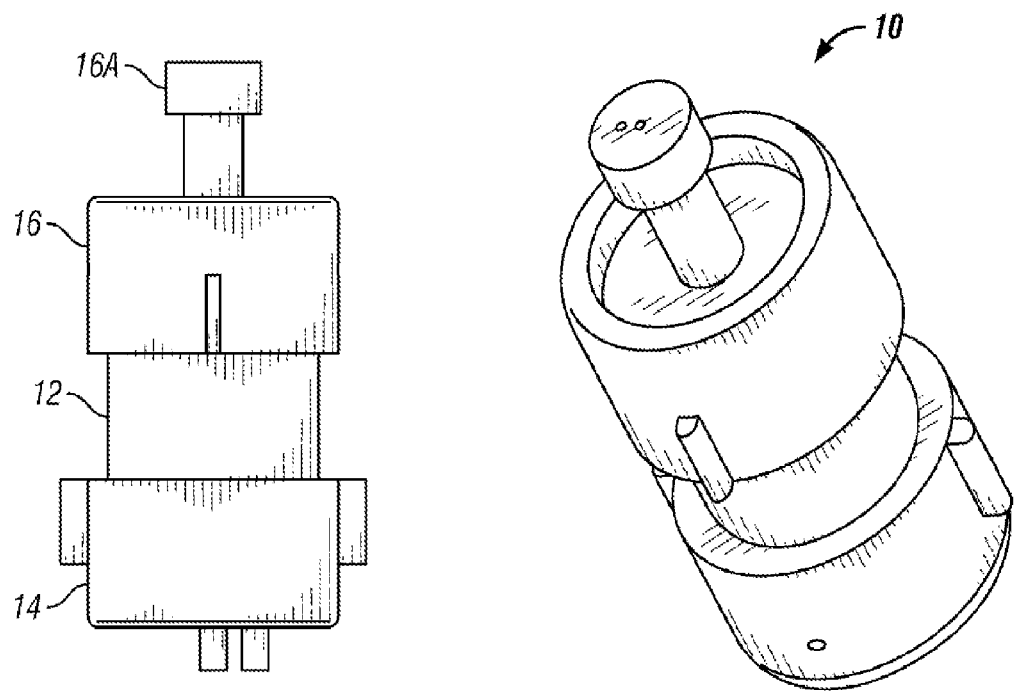
FIG. 6　　　　FIG. 7

WELLBORE FLUID TESTING APPARATUS AND METHODS

BACKGROUND OF THE INVENTION

1. Field of the Invention

The invention relates generally to the field of wellbore construction fluid testing. More specifically, the invention relates to apparatus and methods for testing properties of various fluids used during wellbore construction.

2. Background Art

During the drilling of a wellbore through subsurface rock formations, various fluids are typically used in the well for a variety of functions. The fluids may be circulated through a drill pipe and drill bit into the wellbore, and then may subsequently flow upward through wellbore to the surface. The drilling fluid may act to, among other functions, remove drill cuttings from the bottom of the wellbore to the surface during fluid circulation, suspend drill cuttings and weighting material when fluid circulation is interrupted, control subsurface pressures, maintain the integrity of the wellbore until the exposed portion of the wellbore is cased and cemented, isolate the fluids from the formation by providing sufficient hydrostatic pressure to prevent the ingress of formation fluids into the wellbore, cool and lubricate the drill string and bit, and/or to maximize penetration rate.

In most rotary drilling procedures the drilling fluid takes the form of a "mud," a term of art used to mean a liquid having solids suspended therein. The characteristics of the liquid are selected to and the solids function to impart desired rheological properties to the mud and in certain cases to increase the density thereof in order to provide a suitable hydrostatic pressure at the bottom of the well.

The drilling mud may be either a water-based or an oil-based mud. Drilling mud may consist of, for example, polymers, biopolymers, clays and organic colloids added to a water-based fluid to obtain the required viscosity and filtration properties. High density minerals, such as barite or calcium carbonate, may be added to increase density. Solids from the formation are incorporated into the mud and often become dispersed in the mud as a consequence of drilling. Further, drilling muds may contain one or more natural and/or synthetic polymeric additives, including polymeric additives that increase the rheological properties (e.g., plastic viscosity, yield point, gel strength) of the drilling mud, and polymeric thinners and flocculents. Polymeric additives included in the drilling fluid may act as fluid loss control agents. Fluid loss control agents, such as starch, prevent the loss of fluid to the surrounding formation by reducing the permeability of filter cakes formed on the newly exposed rock surface. In addition, polymeric additives are employed to impart sufficient carrying capacity and thixotropy to the mud to enable the mud to transport the cuttings up to the surface and to prevent the cuttings from settling out of the mud when circulation is interrupted.

International Patent Application Publication No. WO 2008/112795, the underlying patent application for which is owned by the assignee of the present invention, describes a device for testing drilling mud to ensure that the fluid properties are acceptable to the user. An apparatus for testing a drilling fluid as described in the foregoing publication includes a vessel having a fluid inlet, a fluid outlet, and a pair of opposed impermeable platens disposed within the vessel. The apparatus further includes a test fluid container in fluid communication with the fluid inlet, and a collection container in fluid communication with the fluid outlet. Additionally, the disclosed system includes a data acquisition device configured to receive data from at least one of the vessel, the test fluid container, and the collection container.

Another apparatus for testing drilling fluids is described in International Patent Application No. WO 2008/058253, the underlying patent application for which is also owned by the assignee of the present invention. An apparatus described in the foregoing publication includes a vessel having a fluid inlet, a filtrate outlet, a fluid outlet, and at least one permeable medium disposed within the vessel. The system further includes a base fluid container in fluid communication with the fluid inlet, a test fluid container in fluid communication with the fluid inlet, a filtrate container in fluid communication with the filtrate outlet, and a collection container in fluid communication with the fluid outlet. Additionally, the system includes a data acquisition device configured to receive data from at least one of the vessel, the fluid container, the filtrate container, and the collection container.

As described in the foregoing publications, effective fluid loss control is highly desirable to prevent damaging the formation in, for example, completion, drilling, drill-in, displacement, hydraulic fracturing, work-over, packer fluid emplacement or maintenance, well treating, or testing operations. In certain drilling environments, the formation may be exceptionally prone to damage from fluid loss. Examples of such drilling operations may include depleted zone drilling. Depleted drilling zones may be especially prone to fractures (i.e., cracks and disruptions in a formation that may be either naturally formed or induced) Fracturing during the drilling operation, also known as induced fracturing, typically occurs in permeable rocks such as sandstone and carbonates or within impermeable rock typified by shale formations. Induced fracturing is of particular concern when drilling into depleted zones where a drop in pore pressure is anticipated as the reserves decline. In such situations, drilling then becomes more of a technical challenge as the mud weight required to support a section may exceed the tensile strength, or fracture resistance, of the formation. This in turn could lead to increased drilling fluid losses and increased well costs.

One technique under development for drilling in fracture susceptible formations is to dispose a gellable fluid in the wellbore such that it will enter fractures in susceptible formations in liquid form and then undergo state change to a gel. If the liquid state and gel properties are suitable for the particular formation, the fluid will act to seal the fractures and to reduce the incidence of such fractures propagating as drilling resumes, as well as to reduce the incidence of fluid being returned to the wellbore from fractures as they close upon reduction in hydrodynamic pressure when mud circulation is interrupted.

Properties and example compositions of such gellable liquids and test results of using such gellable liquids are described, for example, in Mark S. Aston, et al., *A New Treatment for Wellbore Strengthening in Shale*, paper no. 110713, Society of Petroleum Engineers, Richardson, Tex. prepared for presentation at the 2007 SPE Annual Technical Conference and Exhibition, Anaheim, Calif., Nov. 11-14, 2007.

It is desirable to have an apparatus and method to test fluid properties, in particular gellable liquids, to confirm, for example, their fracture sealing and related mechanical properties (e.g., fracture pressure and compressive strength). While the apparatus disclosed in the two above cited International Patent Application publications are well suited for testing fluid loss and related properties of drilling fluids, they have not proven very useful for testing gellable fluids after the gel has set or cured. In particular, the foregoing described apparatus may be difficult to clean after gel set, and neither apparatus has any features for testing compressive strength or fracture pressure of a set gel. There continues to be a need for an apparatus and method to test properties of various wellbore construction fluids.

SUMMARY OF THE INVENTION

An apparatus according to one aspect of the invention for testing properties of a wellbore fluid includes a test chamber having a first platen and a second platen therein. The test chamber is disposed in a thermally insulating enclosure. The enclosure includes a heating element disposed therein. The platens are configured to simulate response of the wellbore fluid when moved through an hydraulically induced fracture in a subsurface rock formation. The system includes means to control a position of the second platen with respect to the first platen. The system includes a pump for introducing the fluid into a space between the first platen and the second platen and a pump for introducing a fracture pressure test fluid into contact with the wellbore fluid. A respective pressure sensor is in fluid communication with a discharge side of each pump, and a sensor is included to measure a parameter related to the position of the second platen or the space between the platens. A data acquisition and control device is configured to detect signals from the respective pressure transducers and the sensor.

A method for testing a wellbore fluid according to another aspect of the invention includes introducing the fluid in liquid form into an opening in a pressure sealed enclosure. The opening is configured to simulate an hydraulically induced fracture in a subsurface formation while measuring a pressure and volume of the fluid. A fluid loss property of the wellbore fluid is determined from the measured pressure and measured volume.

A method for testing a wellbore fluid according to another aspect of the invention includes introducing the fluid in liquid form into an opening in a pressure sealed enclosure, the opening configured to simulate an hydraulically induced fracture in a subsurface formation while measuring a pressure and volume of the fluid. The fluid is cured into a gel. A fracture test fluid is pumped into contact with the gel while recording a pressure and volume of the fracture test fluid. A fracture pressure of the gel is determined from the measured pressure and volume of the fracture test fluid.

A method for testing a wellbore fluid according to another aspect of the invention includes introducing the fluid in liquid form into an opening in a pressure sealed enclosure. The opening is configured to simulate an hydraulically induced fracture in a subsurface formation. A pressure and volume of the fluid is measured during pumping. The fluid is cured into a gel. A gel breaking agent is introduced into contact with the gel and a property of the wellbore fluid in response to the gel breaking agent.

Other aspects and advantages of the invention will be apparent from the following description and the appended claims.

BRIEF DESCRIPTION OF THE DRAWINGS

FIG. 2 shows an assembled, exterior view of one example of a test chamber used in a system such as shown in FIG. 1.

FIG. 3 shows an example of an upper end cap for the test chamber of FIG. 2, in which a first platen is disposed on an inner surface thereof.

FIG. 4 shows an example of a second platen used in the assembled chamber of FIG. 2.

FIGS. 5, 6 and 7 show various external views of an alternative configuration for a fluid test chamber.

DETAILED DESCRIPTION

Figure 1:
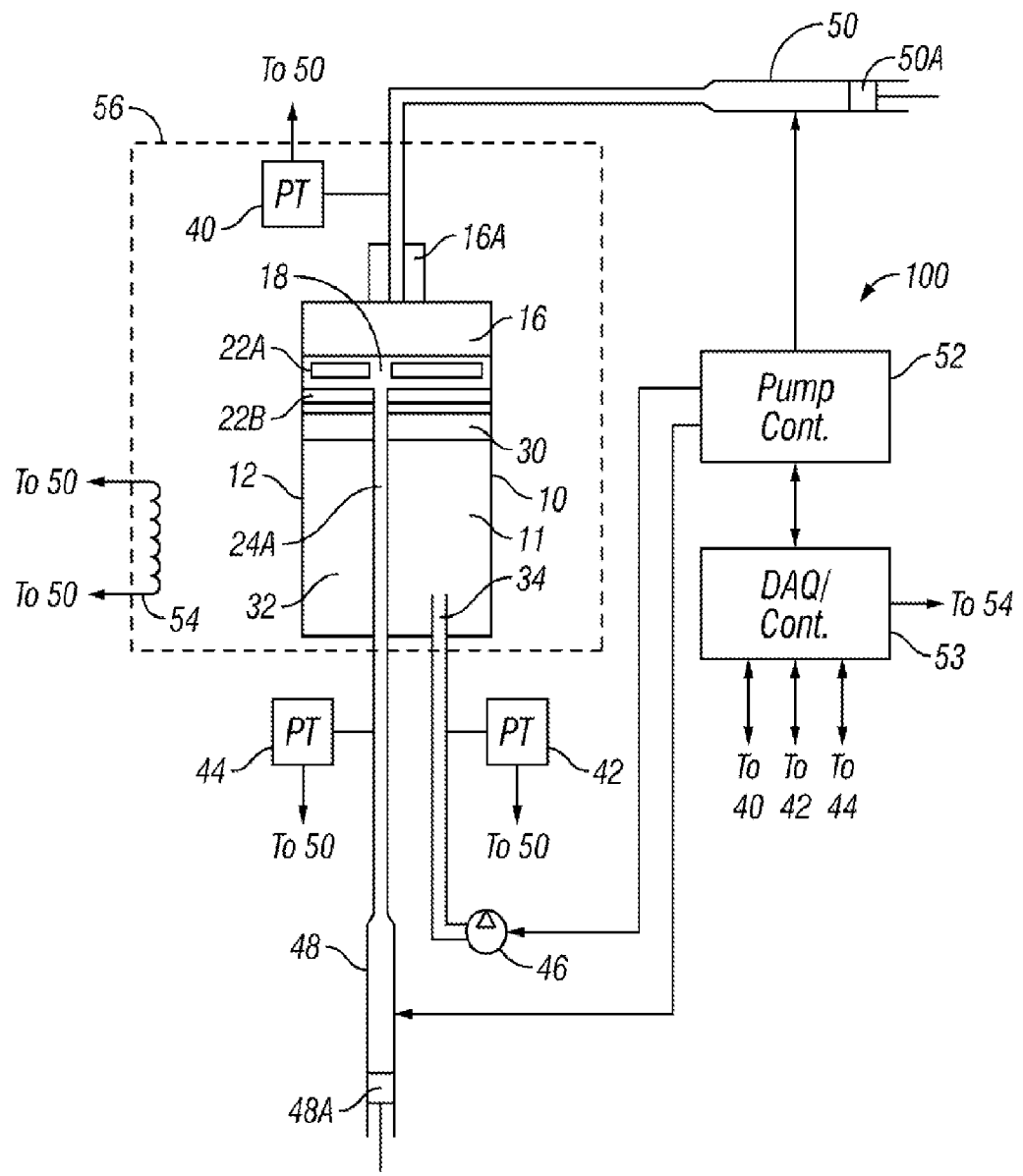
FIG. 1 shows an example gellable fluid test system.

An example system for testing wellbore fluids is shown in FIG. 1. The system 100 includes a pressure-sealed test chamber 10 into which the wellbore fluid is pumped. In some examples, the wellbore fluid is then allowed to cure into gel for further testing. The chamber 10 may be disposed in a thermally insulated enclosure 56. The thermally insulated enclosure 56 may include in its interior a heating element 54 such as an electrical resistance heater for raising the interior of the thermally insulated enclosure 56 to a selected temperature. In some examples, the test chamber 10 includes a void 11 in which electronics, heating elements and/or other small devices useful during testing of wellbore fluids may be placed.

The test chamber 10 is configured internally to simulate a fracture in a subsurface rock formation for purposes of simulating fluid flow therein. To perform such simulating fluid flow function, the test chamber 10 may include an hydraulic chamber enclosure 12, an upper platen 22A disposed against the interior surface of an upper end cap 16 on the hydraulic chamber enclosure 12, and a lower platen 22B disposed on a piston 30 or similar device slidably disposed within the enclosure 12. The piston 30 may be actuated by hydraulic pressure from a pump 46 coupled through an inlet line 34 to an hydraulic cylinder portion 32 of the enclosure 12. The hydraulic cylinder portion is disposed generally below the piston 30 and is used to control the distance between the upper platen 22A and the lower platen 22B as will be further explained. The position of the piston 30 may be controlled, and consequently the distance between the platens 22A, 22B may be controlled, by controlling volume of fluid introduces into the hydraulic cylinder portion 32. Volume control may be performed by monitoring position of the piston 30, for example, by using a position sensor (not shown) such as a linear variable differential transformer, or by monitoring position and/or discharge volume from the hydraulic pump 46. Other devices for controlling piston position will occur to those skilled in the art and the foregoing examples are not intended to limit the scope of the invention. Non-limiting additional examples include a motor-rotated screw and a ball nut coupled to the screw (see, e.g., U.S. Pat. No. 5,438,169 issued to Kennedy et al.), and a linear electrical actuator (see, e.g., U.S. Patent Application Publication No. 2007/0289734 filed by McDonald et al.). In principle, the disclosed hydraulic device performs the functions of controlling the distance between the platens 22A, 22B, and as will be explained further below applying compressive force to the lower platen 22B to cause mechanical compression for further testing the wellbore fluid. Any sensor or combination of sensors that measure a parameter related to the position of the lower platen 22B with respect to the upper platen 22A (or the distance between the platens) can be used in other examples.

Figure 15:
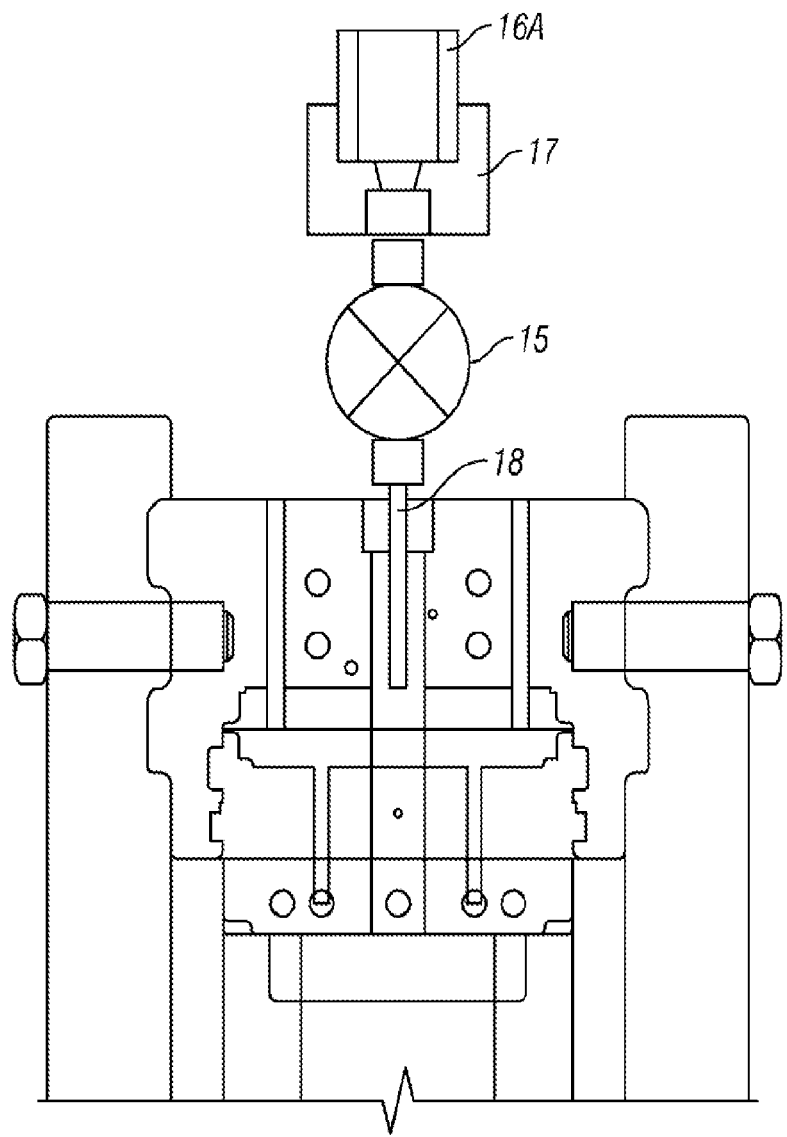
FIG. 15 shows an example of an assembled gellable fluid test system.

The upper platen 22A may include a fluid inlet 18 disposed proximate the center thereof and hydraulically coupled to fluid test sample reservoir 16A that may be disposed on or near the upper end cap 16. The test sample reservoir 16A can store a selected volume of the wellbore fluid being tested, and because of its location within the enclosure 56, such fluid sample will be maintained at the temperature existing inside the enclosure 56. Such temperature may be selected, as will be further explained, to simulate conditions in an actual wellbore. A pump 50 such as a syringe pump may be in hydraulic communication with one end of the test sample reservoir 16A to move the sample out of the reservoir 16A and into the space between the platens 22A, 22B. A syringe pump may be advantageously used in some examples because a volume of fluid discharged by such pump may be readily monitored by monitoring, for example, a linear position of a plunger or piston 50A that acts to displace the fluid from the pump 50. Such position monitoring may be performed, for example by using a position sensor such as a linear variable differential transformer (not shown). Referring to FIG. 15, in some examples, reservoir 16A has a sloped or conical end 17 to prevent material from blocking the line to the upper platen 22A. In some examples, a pressure isolation valve 15 is disposed between reservoir 16A and the inlet 18 to upper platen 22A. The pressure isolation valve 15 operates to isolate the reservoir 16A and the inlet 18 during certain testing processes such as heating. Further, pressure isolation valve 15 allows for test fluid replacements during test sequences or between tests. Other devices to monitor the volume of fluid discharged by the pump 50 will occur to those skilled in the art, and the example described above is not intended to limit the scope of the present invention.

Figure 14:
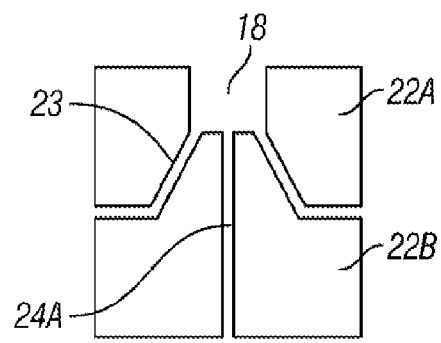
FIG. 14 shows a close up schematic of an example of a portion of an interface between upper and lower platens.

The lower platen 22B may include a passage 24A for pumping a fracture pressure testing fluid into a space between the platens 22A, 22B for testing certain characteristics of the wellbore fluid, for example a gellable fluid after the gel has cured. Such testing fluid may be introduced by a pump 48 such as a syringe pump. Volume of the testing fluid pumped may be monitored, as explained with reference to the wellbore fluid pump 50, for example, by monitoring position of the pump piston 48A. Referring to FIG. 14, the interface between the platens 22A and 22B in the area near inlet 18 and passage 24A may include a corresponding sloped portion 23 in the mating surfaces of 22A and 22B. The sloped portion 23 facilitates the even distribution of test fluid between the surfaces of the platens 22A and 22B.

Each of the foregoing pumps 46, 48, 50 may be in hydraulic communication on the discharge side thereof with a respective pressure transducer 42, 44, 40. The transducers may be in signal communication with a data acquisition and control (DAQ) system 53, which may include a microprocessor (not shown separately) and data mass storage device (not shown separately) for detecting and recording signals generated by the respective transducers (and volume monitoring devices as explained above). Such signal recordings, as will be further explained, may be used to evaluate characteristics of the wellbore fluid being tested in the test chamber 10. Operation of the pumps 46, 48, 50 may be controlled by a pump controller 52, such as a microprocessor-based controller. The pump controller 52 may itself be operated by programming in the DAQ system 53. The DAQ system 53 may also directly or indirectly generate driver current to operate the heating element 54 such that a selected temperature is maintained inside the thermal enclosure 56.

Generally, during operation of the fluid test system 100, a wellbore fluid is introduced into the chamber 10, to the space between the platens 22A, 22B by operation of the test fluid pump 50. The volume of the wellbore fluid may be measured with respect to time using the DAQ system 53 as explained above, and the pressure of the fluid may be measured using signals from the respective pressure transducer 40. The dimension (thickness) of the space between the platens 22A, 22B may be maintained by application of a selected hydraulic pressure from the hydraulic pump 46.

After the space between the platens 22A, 22B is filled with test wellbore fluid (and in some examples after certain testing takes place), in some examples the fluid is allowed to or is caused to cure into a gel. In one example, gel cure can be initiated by maintaining a selected temperature in the thermally insulated chamber 56. In other examples, gel cure may be initiated chemically, or by application of radiation such as ionizing radiation, ultraviolet radiation, electron beam radiation or other electromagnetic radiation. In still other examples, gel cure may be initiated by applying acoustic energy or be dewatering. After the gel has cured, various additional tests may be performed thereon. For example, the hydraulic pressure on the piston 30 may be increased so as to test the compressive strength of the gel. In another example, fluid may in introduced through the passage 24A in the lower platen 22B by operating test fluid pump 48, while monitoring volume discharged therefrom and pressure using signals from transducer 44. The fluid introduced through such passage 24A may be used to test the fracture strength of the gel. The gel may be further tested for resistance to thermal degradation, for example, by increasing the temperature inside the thermally isolated enclosure 56 and thus the test chamber 10.

FIG. 2 shows an assembled view of one example of the test chamber 10 used with a system such as shown in FIG. 1. The test chamber 10 may include an upper end cap 16 and a lower end cap 14 affixed to longitudinal ends of the chamber enclosure 12. The chamber enclosure 12 may be in the form of an annular cylinder, and made from steel or other high strength material configured to resist internal pressures used in testing fluids as will be further explained herein. The chamber enclosure 12 in the present example may include an integrally formed flange 12A, 12B on each longitudinal end. The flanges 1A, 12B are configured to sealingly engage a corresponding surface of the upper end cap 16 and the lower end cap 14, respectively. The end caps 16, 14 may be removably affixed to the respective flanges 12A, 12B using cap screws 20 or the like. The upper end cap 16 may include a port 18 to enable pumping therein of the fluid to be tested. Fluid entering the space between the platens through the port 18 may leave the space around the perimeter of the first platen (22A in FIG. 1).

Referring to FIG. 3, an interior view of the upper end cap 16 includes disposed against its interior surface the first platen 22A, which in the present example may be a corrugated aluminum disk. The first platen 22A provides a surface representative of one side of an hydraulic fracture formed in a subsurface formation. As shown in FIG. 3, the port 18 extends through a center of the first platen 22A to enable flow therethrough. A corresponding second platen is shown in FIG. 4 at 22B. The second platen 22B may also be in the form of a corrugated aluminum disk and may include a centrally disposed passage 24 to enable pumping of a fracture pressure test fluid into contact with the gel after cure (explained further below). The platens 22A, 22B may include one or more radially extending grooves (not shown) on the surfaces thereof to facilitate even spatial distribution of test fluid and any suspended solids therein.

Another example of the test chamber 10 is shown in horizontal side view in FIG. 5, in vertical side view in FIG. 6, and in oblique view in FIG. 7. The example test chamber 10 in FIGS. 5, 6, and 7 may have substantially the same internal components as shown in and as explained with reference to FIGS. 2, 3 and 4, however in the present example, the end caps 16, 14 may be secured to the chamber enclosure 12 using threads as shown in the figures, of any type known in the art for securing caps to a pressure sealed enclosure. Functionally, the test chamber 10 in the present example may be the same as in the previously described example.

Figure 8:
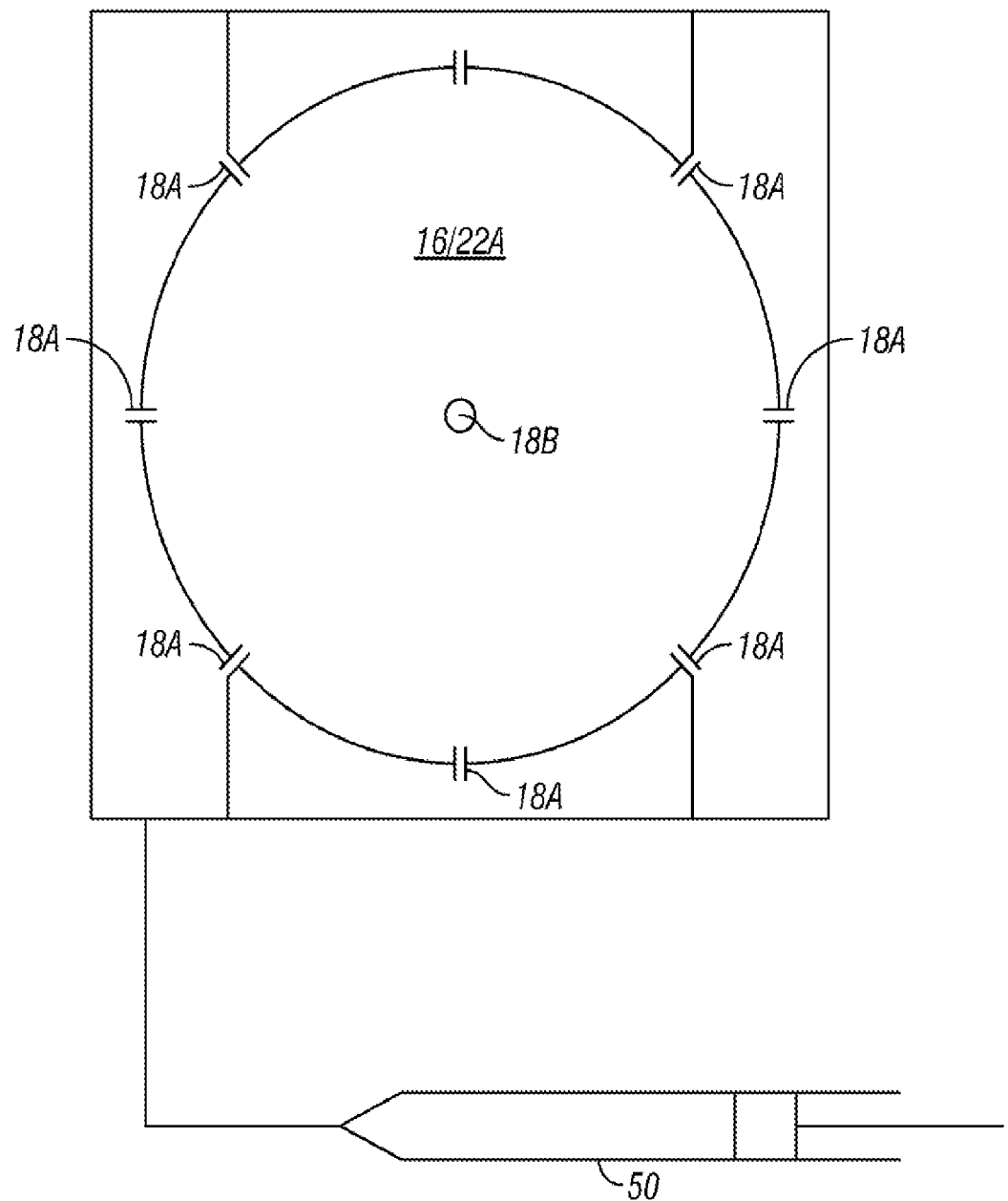
FIG. 8 shows an alternative end cap and upper platen configuration.

Another example of the upper platen and upper end cap are shown in FIG. 8. It may be advantageous for testing gellable fluids to assure that the gel substantially fills the entire space between the upper platen 22A and the lower platen (22B in FIG. 2). In the example of FIG. 8, the end cap 16 and the upper platen 22A include a plurality of fluid inlets 18A disposed about the perimeters thereof. A fluid discharge port 18B may be disposed approximately in the center of the platen 22A and end cap 16.

As an alternative to the platen and end cap shown in FIG. 8, in some examples an equivalent result, namely substantial filling of the entire space between platens, may be obtained by initiating pumping the test fluid while the space between platens is maintained at an initial value. After the space is substantially filled, the space may be reduced in thickness by suitably operating the piston (30 in FIG. 1). Testing may then continue by pumping the test fluid and monitoring pressure.

Figure 9:
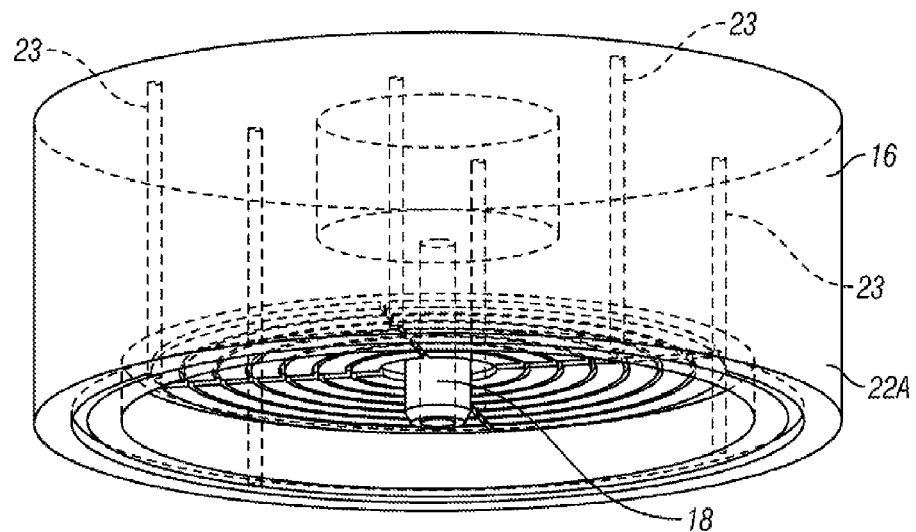
FIG. 9 shows another example of an end cap and upper platen.
Figure 10:
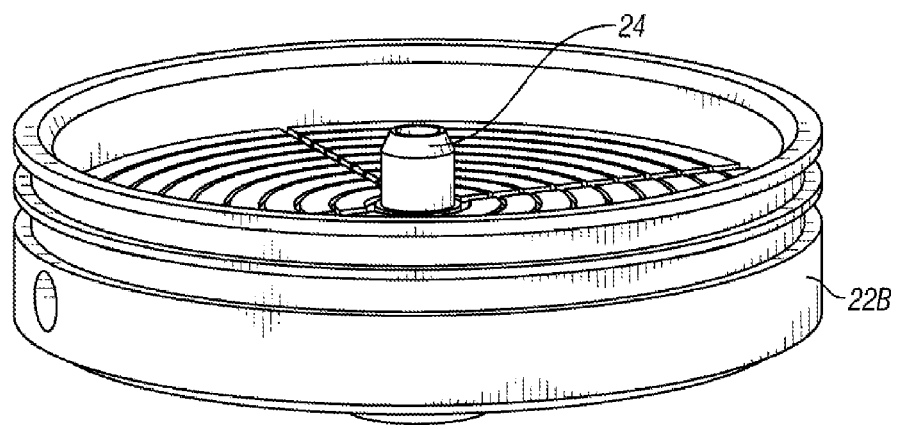
FIG. 10 shows a corresponding example of a lower platen that may be used with the upper platen in FIG. 9.

Another example of the end cap and upper platen is shown in FIG. 9. The example in FIG. 9 may include a plurality of fluid loss exit ports 23 disposed about the perimeter of the upper platen 22A and arranged to enable fluid to be removed from the wellbore fluid sample by testing. FIG. 10 shows a corresponding example of the lower platen 22B including a fluid entry port 24 or passage in the center thereof.

Operating the system described above, and once again referring to FIG. 1, may include the following. The piston 30 may be moved by operating hydraulic pump 46 until a distance (thickness) between the upper platen 22A and the lower platen 22B is at a selected value. The test fluid may then be introduced into the chamber 10 by operating pump 50.

Figure 11:
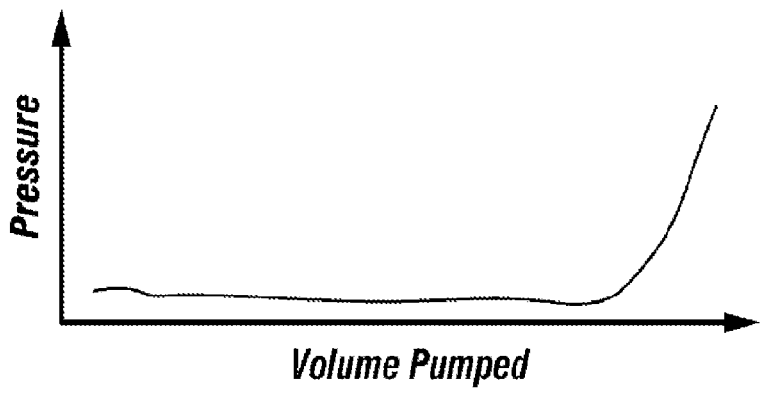
FIG. 11 shows a graph of pressure with respect to pumped volume of wellbore fluid for fluid loss testing thereof.

In one example, if the test fluid includes suspended solids for the purpose of controlling fluid loss into permeable formations, and referring to FIG. 11, a fluid loss test may be performed during introduction of the test fluid by measuring pressure thereof during the pumping (e.g., using signals from transducer 40). It is expected that as the solids adhere to the platens 22A, 22B, eventually a substantially impermeable filter cake will be deposited on the platens. At such time, the measured pressure can be expected to substantially increase as additional fluid is pumped. Such is shown in the graph of FIG. 11. In another example and with further reference to FIG. 1, and as explained above, during pumping, the distance between platens may be set to a first value. Fluid may be pumped until it is inferred that the space is filled. For example, evidence of fluid appearing at the fluid discharge (e.g., 18A in FIG. 8) may be used to infer filling of the space. The distance may be subsequently reduced by operating the piston 30. Fluid pumping may continue as explained with reference to FIG. 12.

After such fluid loss testing is completed, or for gellable fluids for which no such testing is to be performed, after the space between the platens is filled, the gel may be cured. Curing may be performed as explained above, and may include as non-limiting examples, chemical, thermal and/or radiation curing. It may be desirable to be able to determine whether the gel is cured for further testing. In one example, the gellable liquid can be determined to be cured into a gel when it has a non-zero equilibrium modulus. There are two alternative ways of stating the same principle concerning zero-equilibrium modulus: (a) that the gel should not relax under a small mechanical stress even if applied for an infinitely long time; or (b) that the gel should not flow under the action of a mechanical stress imposed for an infinite period of time. A more detailed explanation of the foregoing example may be obtained at the Uniform Resource Locator, http://complexfluids.umd.edu/papers/bk2_2005.pdf, the content of which publication is incorporated herein by reference for all purposes.

In another example, the gellable liquid can be determined to be cured into a gel when it has a substantially non-zero shear modulus. One example of a way to determine such state is when the gel will transmit shear acoustic waves, because liquids generally have zero shear modulus and substantially do not transmit shear acoustic waves.

Figure 12:
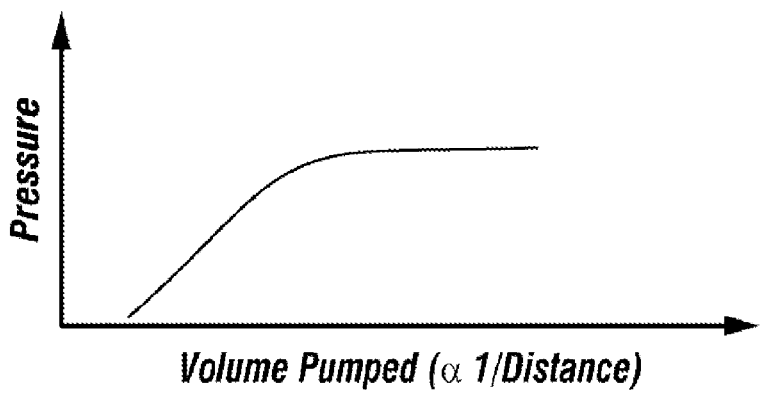
FIG. 12 shows a graph of pressure of hydraulic fluid with respect to pumped volume thereof for compressive strength testing.

After cure of the gel, testing mechanical properties of the gel may include the following. First, and referring to FIG. 12, compressive strength testing may be performed by applying closure pressure on the gel. Such closure pressure may be applied by operating the piston (30 in FIG. 1) using hydraulic pressure from the hydraulic pump (46 in FIG. 1). Generally, as the distance between platens is closed by moving the piston, the gel will be compressed. Hydraulic pressure (e.g., measured by transducer 42) will increase as the distance closes. Distance closure may be inferred, for example, by measuring the volume of pumped hydraulic fluid. At the time the compressive strength of the gel is exceeded, continued closure of the distance will result, for example, in gel extrusion. Such is shown in FIG. 12, for example, by small or no increase in hydraulic pressure while volume of hydraulic fluid increases.

Figure 13:
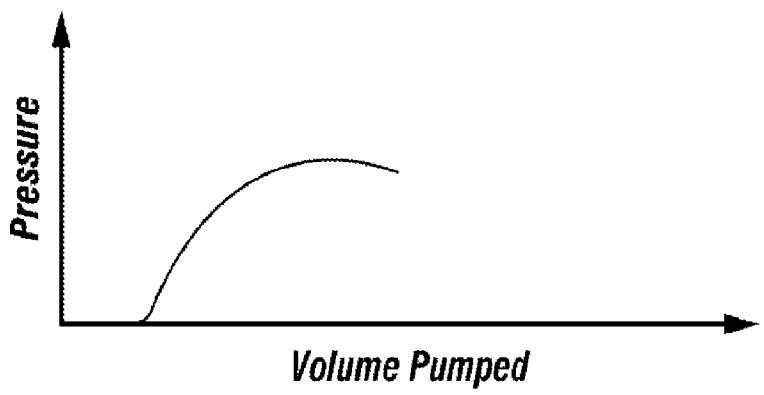
FIG. 13 shows a graph of pressure with respect to volume pumped of fracture strength testing fluid for testing fracture strength of a gel.

It is also possible to test the fracture strength of the gel after cure. Such testing may be performed by introducing fluid into the passage (24A in FIG. 1) through the lower platen to hydraulically compress the gel, such as by operating the pump (48 in FIG. 1). Referring to FIG. 13, the volume of pumped fluid and the pressure thereof are monitored during pumping. When the fracture strength of the gel is exceeded, continued fluid pumping may result in steady or even lower pressure, as shown in the graph of FIG. 13.

In other examples, a permeable subsurface formation may be simulated. In such examples, the aluminum platens (22A, 22B in FIG. 1) may be substituted by similarly shaped disks made of samples of permeable rock formation. Other formations may be simulated by substituting, for example, disks made from powdered and/or pelletized aluminum oxide. Still other examples may include disks made from epoxy/glass bead composite materials.

In other examples, the above described apparatus may be used to test properties of other fluids such as drilling mud. In still other examples, fluids such as dewatering fluids may be similarly tested. An example of such fluid is sold under the trademark FORM-A-SQUEEZE, which is a registered trademark of the assignee of the present invention.

In another aspect of the invention, properties of certain breakable gels, and chemicals used to break such gels may be tested using an apparatus as explained with reference to FIG. 1. In the present example, a gellable liquid may be introduced into the sample chamber in liquid form, substantially as explained above. The gel may be allowed to or caused to cure as explained above. After gel cure, a gel breaking agent may be introduced into the gel, typically (but not limited to) through the port in the lower platen (22B in FIG. 1). Testing to determine breakage of the gel may include, for example, pumping additional fluid from the wellbore fluid pump (50 in FIG. 1) and measuring the pressure to pump the additional wellbore fluid, reducing the distance between the platens and measuring the pressure required to reduce the distance, or pumping fluid through the port (24 in FIG. 1) in the lower platen using the fracture pressure test pump (48 in FIG. 1).

An apparatus according to the present invention advantageously can test wellbore fluids for properties related to their capacity to seal hydraulically induced fractures in subsurface rock formations during wellbore drilling and their capacity to resist fracture closing and other failure to maintain wellbore integrity. The apparatus of the present invention is also usable for the purpose of testing fluid loss properties of well drilling fluids as do apparatus known in the art prior to the present invention. The apparatus of the invention can therefore provide more types of fluid testing capability than prior testing apparatus, and may eliminate the need for more than one type of fluid testing apparatus. Methods according to the invention may enable optimizing properties of wellbore fluids such as gellable wellbore fluids for the particular formations being drilled and for the particular subsurface conditions (e.g., overburden and fluid pressure, and temperature) encountered.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An apparatus for testing properties of a wellbore fluid, comprising:
    a test chamber having a first platen and a second platen therein, the platens configured to simulate response of the fluid when moved through an hydraulically induced fracture in a subsurface rock formation;
    means for controlling a position of the second platen with respect to the first platen during testing;
    a pump for introducing the wellbore fluid into a space between the first platen and the second platen;
    a pump for introducing a pressure test fluid into contact with the wellbore fluid;
    a respective pressure sensor in fluid communication with a discharge side of each pump and a sensor configured to measure a parameter related to position of the second platen;
    a thermally insulated enclosure in which the test chamber is disposed;
    a heater for maintaining a selected temperature in the enclosure; and
    a data acquisition and control device configured to detect signals from the respective pressure transducers and the sensor.

2. The apparatus of claim 1 wherein the first and second platens comprise corrugated aluminum.

3. The apparatus of claim 1 wherein the first and second platens comprise rock formation.

4. The apparatus of claim 1 wherein the first and second platens comprise one of powdered aluminum oxide and epoxy/glass bead composite material.

5. The apparatus of claim 1 wherein the first and second platens are shaped as disks.

6. The apparatus of claim 1 wherein the first and second platens are shaped as corresponding cones.

7. The apparatus of claim 1 wherein the test chamber is disposed in a pressure sealed enclosure.

8. The apparatus of claim 7 wherein the enclosure is sealed at at least one longitudinal end thereof by an end cap, the end cap affixed to the enclosure by at least one of threaded couplings and capscrews.

9. The apparatus of claim 8 wherein the end cap includes a plurality of fluid inlets on an outer perimeter thereof in fluid communication with the pump for introducing the gellable fluid, the end cap including a fluid outlet in a center thereof.

10. The apparatus of claim 1 wherein the means for controlling position comprises an hydraulic cylinder and a piston disposed therein.

11. The apparatus of claim 1 further comprising a reservoir in fluid communication with a test fluid passage in the first platen and with the pump for introducing the wellbore fluid into the space, the reservoir disposed within the thermally insulated enclosure such that the wellbore fluid is introduced into the space at the temperature inside the enclosure.

12. A method for testing a wellbore fluid, comprising:
    introducing the fluid in liquid form into an opening in a pressure sealed enclosure, the opening configured to simulate an hydraulically induced fracture in a subsurface formation while measuring a pressure and volume of the fluid;
    maintaining the fluid at a selected temperature; and
    determining a fluid loss property of the fluid from the measured pressure and measured volume.

13. The method of claim 12 further comprising:
    curing the fluid into a gel;
    pumping a fracture test fluid into contact with the gel while recording a pressure and volume thereof; and
    determining a fracture pressure of the gel from the measured pressure and volume of the fracture test fluid.

14. The method of claim 13 wherein the fracture pressure is determined when a rate of pressure increase of the fracture pressure test fluid changes substantially with respect to the measured volume thereof.

15. The method of claim 12 further comprising reducing a size of the opening while measuring a parameter related to the size, and determining a compressive strength of the gel from the measured parameter related to size.

16. The method of claim 15 wherein the compressive strength is determined when a rate of change of the measured parameter related to size varies substantially.

17. The method of claim 16 wherein the parameter related to size comprises a pressure and a volume of an hydraulic fluid used to operate a piston coupled to a platen.

18. The method of claim 12 wherein the fluid is curable from liquid form into a gel by at least one of chemical curing, temperature curing and radiation curing.

19. The method of claim 12 further comprising setting a size of the opening to a first value, introducing the fluid into the opening in liquid form, and reducing the size of the opening while continuing the introducing.

20. The method of claim 13 further comprising introducing a gel breaking agent into contact with the gel and measuring a property of the wellbore fluid in response to the gel breaking agent.

21. A method for testing a gellable wellbore fluid, comprising:
    introducing the gellable fluid in liquid form into an opening in a pressure sealed enclosure, the opening configured to simulate an hydraulically induced fracture in a subsurface formation while measuring a pressure and volume of the gellable fluid;

curing the fluid into a gel;

pumping a fracture test fluid into contact with the gel while recording a pressure and volume thereof; and determining a fracture pressure of the gel from the measured pressure and volume of the fracture test fluid.

22. The method of claim 21 wherein the fracture pressure is determined when a rate of pressure increase of the fracture pressure test fluid changes substantially with respect to the measured volume thereof.

23. The method of claim 21 further comprising reducing a size of the opening while measuring a parameter related to the size, and determining a compressive strength of the gel from the measured parameter related to size.

24. The method of claim 23 wherein the compressive strength is determined when a rate of change of the measured parameter related to size varies substantially.

25. The method of claim 24 wherein the parameter related to size comprises a pressure and a volume of an hydraulic fluid used to operate a piston coupled to a platen.

26. The method of claim 21 wherein the fluid is curable from liquid form into a gel by at least one of chemical curing, temperature curing, acoustic curing and radiation curing.

27. The method of claim 21 further comprising setting a size of the opening to a first value, introducing the fluid into the opening in liquid form, and reducing the size of the opening while continuing the introducing.

28. A method for testing a wellbore fluid, comprising:

introducing the fluid in liquid form into an opening in a pressure sealed enclosure, the opening configured to simulate an hydraulically induced fracture in a subsurface formation while measuring a pressure and volume of the fluid;

curing the fluid into a gel;

introducing a gel breaking agent into contact with the gel; and measuring a property of the wellbore fluid in response to the gel breaking agent.

* * * * *